(12) United States Patent
Voerman

(10) Patent No.: US 11,065,405 B2
(45) Date of Patent: Jul. 20, 2021

(54) ELECTRONIC CIGARETTE, AND METHOD OF CLEANING AN ELECTRONIC CIGARETTE

(71) Applicant: JT International S.A., Geneva (CH)

(72) Inventor: Dick Paul Voerman, Zwolle (NL)

(73) Assignee: JT International S.A.

( * ) Notice: Subject to any disclaimer, the term of this patent is extended or adjusted under 35 U.S.C. 154(b) by 467 days.

(21) Appl. No.: 16/091,416

(22) PCT Filed: Apr. 4, 2017

(86) PCT No.: PCT/NL2017/050209
§ 371 (c)(1),
(2) Date: Feb. 19, 2019

(87) PCT Pub. No.: WO2017/176113
PCT Pub. Date: Oct. 12, 2017

(65) Prior Publication Data
US 2019/0281894 A1    Sep. 19, 2019

(30) Foreign Application Priority Data

Apr. 4, 2016 (NL) ..................... 2016546

(51) Int. Cl.
| | |
|---|---|
| *A61M 15/06* | (2006.01) |
| *B08B 7/00* | (2006.01) |
| *H05B 1/02* | (2006.01) |
| *H05B 3/14* | (2006.01) |
| *H05B 3/04* | (2006.01) |
| *H05B 3/44* | (2006.01) |

(Continued)

(52) U.S. Cl.
CPC ............ *A61M 15/06* (2013.01); *A24F 40/46* (2020.01); *A61M 11/042* (2014.02);
(Continued)

(58) Field of Classification Search
CPC ... A61M 11/042; A61M 15/06; B08B 7/0071; H05B 3/04; H05B 3/44
See application file for complete search history.

(56) References Cited

U.S. PATENT DOCUMENTS

2007/0267031 A1   11/2007  Hon
2011/0236002 A1    9/2011  Oglesby et al.
(Continued)

FOREIGN PATENT DOCUMENTS

| EA | 009116 B1 | 10/2007 |
|---|---|---|
| GB | 2524856 A | 10/2015 |

(Continued)

OTHER PUBLICATIONS

Wikipedia, "Aluminum nitride" via https://en.wikipedia.org/wiki/Aluminium_nitride ; pp. 1-6 (Year: 2021).*
(Continued)

*Primary Examiner* — Binh X Tran
(74) *Attorney, Agent, or Firm* — Lerner, David, Littenberg, Krumholz & Mentlik, LLP

(57) ABSTRACT

An electronic cigarette includes a ceramic heating element having a current conducting heating member on and/or in a body of ceramic material which is impenetrable to the liquid; a liquid delivery member to deliver liquid from a liquid storage to the heating element; a battery; and an electric circuit for electrically connecting the heating element to the battery. The body of ceramic material is to contact or be in close proximity to the liquid delivery member, to vaporize the liquid when the ceramic heating element produces heat. The electronic cigarette further includes a cartomizer part, having the liquid storage and the liquid delivery member, and a battery holding part, having the battery, the ceramic heating element, and the electric circuit. In an assembled state, the cartomizer part and the battery holding part are assembled. In a disassembled state, the cartomizer part and the battery holding part are separated.

13 Claims, 3 Drawing Sheets

(51) Int. Cl.
*A61M 11/04* (2006.01)
*A24F 40/46* (2020.01)
A61M 16/00 (2006.01)
A24F 40/10 (2020.01)

(52) U.S. Cl.
CPC ......... *B08B 7/0071* (2013.01); *H05B 1/0297* (2013.01); *H05B 3/04* (2013.01); *H05B 3/141* (2013.01); *H05B 3/44* (2013.01); *A24F 40/10* (2020.01); *A61M 2016/0021* (2013.01); *A61M 2205/3646* (2013.01); *A61M 2205/3653* (2013.01); *A61M 2205/8206* (2013.01); *A61M 2205/8243* (2013.01); *A61M 2207/00* (2013.01); *A61M 2209/10* (2013.01); *H05B 2203/021* (2013.01); *H05B 2203/022* (2013.01)

(56) References Cited

U.S. PATENT DOCUMENTS

2017/0347714 A1* 12/2017 Metz .................. A24F 40/46
2018/0049471 A1* 2/2018 Holoubek ............ A24F 40/465
2018/0116284 A1* 5/2018 Biel .................... A24F 40/48
2018/0317550 A1* 11/2018 Zhu .................... A24B 15/167
2020/0120983 A1* 4/2020 Chen .................. A61M 11/042

FOREIGN PATENT DOCUMENTS

WO    9823171 A1    6/1998
WO    2015031836 A1    3/2015

OTHER PUBLICATIONS

Wikipedia, "Aluminum oxide" via https://en.wikipedia.org/wiki/Aluminium_oxide ; pp. 1-10 (Year: 2021).*
Wikipedia, Silicon nitride via https://en.wikipedia.org/wiki/Silicon_nitride ; pp. 1-11 (Year: 2021).*
International Search Report and Written Opinion dated Jul. 3, 2017 for Application No. PCT/NL2017/050209.
Search Report dated Aug. 25, 2016 for Application No. NL 2016546.

* cited by examiner

ELECTRONIC CIGARETTE, AND METHOD OF CLEANING AN ELECTRONIC CIGARETTE

CROSS-REFERENCE TO RELATED APPLICATIONS

The present application is a national phase entry under 35 U.S.C. § 371 of International Application No. PCT/NL2017/050209, filed Apr. 4, 2017, published in English, which claims priority to Netherlands Patent Application No. 2016546 filed April 4, 2016, the disclosures of which are incorporated herein by reference.

FIELD OF THE INVENTION

The invention relates to the field of electronic cigarettes. In an aspect, the invention relates to an electronic cigarette comprising a cartomizer part and a battery holding part. The invention further relates to a method of cleaning an electronic cigarette.

BACKGROUND OF THE INVENTION

Reference US 2015/0296887 A1 discloses an electronic cigarette having a heating element comprising a ceramic rod which may be solid or hollow, for mounting a heating wire on and/or in the ceramic rod. The ceramic rod functions as a liquid transport member for transporting liquid from a liquid storage chamber to a heated zone of the heating element to vaporize the liquid to produce vapor to be inhaled by a user. The electronic cigarette according to said reference is a one piece item.

Other types of electronic cigarettes may be assembled from different parts which, when used to smoke, are in an assembled state. In some embodiments of the multi-part electronic cigarette, one part of the electronic cigarette may be a battery holding part comprising a rechargeable or non-rechargeable battery. In a disassembled state, i.e. when the battery holding part has been separated from the remainder of the electronic cigarette, the battery holding part may be connected to a power source for recharging the battery (in case of a rechargeable battery), or the battery may be exchanged (in case of a non-rechargeable battery). Another part of the multi-part electronic cigarette may be a liquid holding part, sometimes also referred to as cartomizer, comprising a liquid storage. In a disassembled state, i.e. when the liquid holding part has been separated from the remainder of the electronic cigarette, the liquid storage may be refilled, or the liquid holding part may be replaced as a whole for ease of use, and/or for a different taste experience in case of another liquid flavor.

A problem in the art as illustrated in the above reference is that, during use of the electronic cigarette, a pollution of the heating element takes place. This pollution is caused by constituents of the vaporizing liquid burning on the high temperature heating wire of the heating element, and burning in the capillary ducts or pores of the ceramic rod, in particular at locations near the heating wire. During prolonged activation of the heating element, temperature at and near the heating wire tends to even rise higher, giving rise to more burning.

Accordingly, negative effects of an increased temperature of the heating element are an increased burning of the vaporizing liquid, and an increased pollution. Toxic gases may be released.

Furthermore, more generally, in some embodiments of the liquid transport member, in particular if it is a wick made of a material having a relatively low ignition temperature, an increased temperature of the heating element in combination with a wick which is insufficiently wetted by the vaporizing liquid may lead to overheating of the wick, or the wick catching fire, which is a potentially very dangerous situation for a user, and anyway spoils the smoking experience of the user. Another negative effect is that an once overheated wick has a decreased wicking capacity.

A negative effect of the pollution is that it fouls the taste of the vapor, which is detrimental to the user's smoking experience. This negative taste effect exists not only during an initial burning of the vaporizing liquid, but also during subsequent draws on the electronic cigarette when the negative taste effect comes from the same burnt material heating up again.

Another negative effect of this pollution is that it clogs the capillary ducts or pores of the liquid transporting member, to thereby reduce the liquid transporting capacities of the liquid transporting member and, as a result, reduce the vapor producing capacity thereof.

SUMMARY OF THE INVENTION

It would be desirable to provide an electronic cigarette wherein the effects of pollution resulting from burnt vaporizing liquid are reduced.

To address this concern, in a first aspect of the invention electronic cigarette is provided, comprising: a liquid storage; a heating element; a liquid delivery member configured to deliver liquid from the liquid storage to the heating element; a battery; and an electric circuit configured to electrically connect the heating element to the battery for the heating element to produce heat, and further configured to electrically disconnect the battery from the heating element. The heating element is a ceramic heating element comprising a current conducting heating member on and/or in a body of ceramic material, the body of ceramic material being impenetrable to the liquid. The body of ceramic material is configured to heat the liquid delivered by the liquid delivery member to vaporize the liquid when the ceramic heating element produces heat. The electronic cigarette comprises a cartomizer part, comprising the liquid storage and the liquid delivery member, and a battery holding part, comprising the battery, the ceramic heating element and the electric circuit. The electronic cigarette is configured to be brought in an assembled state in which the cartomizer part and the battery holding part are assembled, and in a disassembled state in which the cartomizer part and the battery holding part are separated from one another.

This allows for moving the body of ceramic material and the liquid delivery member away from each other to a distance at which the liquid delivered by the liquid delivery member is not vaporized when the ceramic heating element produces heat. It has appeared that the heating as such leads to a rapid removal of any pollution on the surface of the body of ceramic material, in particular burnt remains of the vaporizing liquid. The pollution simply evaporates, and thus the electronic cigarette is cleaned. This cleaning can be easily performed by the user after some time of use, just by moving the body of ceramic material away from the liquid delivery member, and activating the ceramic heating element to evaporate the pollution.

When the cartomizer part has been separated from the battery holding part, the ceramic heating element has been moved away from the liquid delivery member. Activating the ceramic heating element in such a situation provides for the cleaning of the body of ceramic material.

The liquid delivery member may be a wick. In other embodiments, the liquid delivery member may comprise at least one porous or capillary element. In still other embodiments, the liquid delivery member may be a liquid transporting mechanism, such as a jetting mechanism, for transporting a quantity of liquid to the ceramic heating element. The quantity of liquid may be a volume of liquid delivered in droplets.

The ceramic heating element of the electronic cigarette has a body of ceramic material which is impenetrable to the vaporizing liquid. This body of ceramic material is different from the liquid delivery member. Moreover, the body of ceramic material does not comprise capillary ducts for the vaporizing liquid.

An advantage of the body of ceramic material which is impenetrable to the vaporizing liquid is that no building up of pollution can take place inside the ceramic material of the body. Thus, a taste experience of a user of the electronic cigarette is improved.

In an embodiment of the electronic cigarette, the body of ceramic material is configured to contact the liquid delivery member, or to be in close proximity to the liquid delivery member. Since the heating member of the ceramic heating element heats the body of ceramic material, any excess temperature at the heating member itself is levelled out at the surface of the body of ceramic material where a relatively even temperature is provided when the heating element is activated.

In an embodiment, the electronic cigarette further comprises a separating structure for moving the body of ceramic material and the liquid delivery member away from each other to a distance at which the liquid delivered by the liquid delivery member is not vaporized when the ceramic heating element produces heat.

Here, a separating structure is a coupling/decoupling mechanism for coupling/decoupling the cartomizer part and the battery holding part. When the cartomizer part has been decoupled (separated) from the battery holding part, the ceramic heating element has been moved away from the liquid delivery member.

In an embodiment of the electronic cigarette, the electric circuit comprises an electric switch operable to electrically connect the battery to the ceramic heating element, and further operable to electrically disconnect the battery from the heating element.

If the electronic cigarette comprises a battery holding part, the electric switch may be provided on the battery holding part. The electric switch may be manually operated. The electric switch is used to activate the ceramic heating element to produce heat, by connecting the battery to the (heating member of the) ceramic heating element.

Although the present invention allows for a cleaning the surface of the body of ceramic material multiple times through activating the ceramic heating element to produce heat, when the body of ceramic material and the liquid delivery member are at a distance from each other at which the liquid delivered by the liquid delivery member is not vaporized when the ceramic heating element produces heat, the cleaning effect of this procedure decreases with every next cleaning procedure, until the surface of the body of ceramic material becomes polluted to an extent that the battery holding part should be discarded. At such time, the battery of the battery holding part may still allow further use for heating the ceramic heating element.

In an embodiment of the electronic cigarette, the electric circuit comprises an electric connector, wherein the connector is configured to connect the ceramic heating element to the electric circuit when the ceramic heating element is mounted in the battery holding part, and wherein the connector is further configured to disconnect the ceramic heating element from the electric circuit when the ceramic heating element is removed from the battery holding part. The electric connector allows for a removal of the ceramic heating element from the battery holding part, whereafter another ceramic heating element, such as a new, unused ceramic heating element, may be mounted in the battery holding part. In this way, the use life of the battery holding part can be extended, since the battery of the battery holding part may then continue to heat the other ceramic heating element.

In an embodiment of the electronic cigarette comprising the connector, the battery holding part comprises a ceramic heating element removal structure for facilitating a removal of the ceramic heating element from the battery holding part. The ceramic heating element may be clamped in an opening, such as an end opening, of the battery holding part. In the opening, the ceramic heating element is held by friction, and electric terminals of the ceramic heating element are held by friction by the connector. The ceramic heating element removal structure may comprise a hole or recess in the battery holding part for inserting a tool to move the ceramic heating element out of the opening, thereby releasing the electric terminals of the ceramic heating element from the connector.

In an embodiment of the electronic cigarette, the ceramic heating element has a positive temperature coefficient of electrical resistance. As a result, the electrical resistance of the ceramic heating element increases with increasing temperature, to thereby decrease the current flowing in the ceramic heating member. A decrease of current leads to a lowering of the heat production in the ceramic heating element, and a corresponding decrease of temperature. This self-stabilizing effect of the ceramic heating element leads to a maintaining of a desired temperature of the ceramic heating element, even at prolonged activation of the ceramic heating element. With a proper thermal design, the temperature can be held to a level where burning of the vaporizing liquid is held low, or is largely of wholly prevented, and where a risk of overheating of the liquid delivery member, which in case of a wick may lead to degradation of the wick and the wick catching fire, is largely or wholly prevented.

In an embodiment of the electronic cigarette, the ceramic material comprises aluminum nitride, AlN, alumina, $Al_2O_3$, or silicon nitride, $Si_3N_4$.

It has been found that these ceramic materials are impenetrable to the vaporizing liquid, and show the cleaning effect of evaporating burnt vaporizing liquid from its surface when the ceramic heating element is activated at a distance from the liquid delivery member at which the liquid delivered by the liquid delivery member is not vaporized when the ceramic heating element produces heat.

In an embodiment of the electronic cigarette, the ceramic heating element comprises a co-fired ceramic, in particular a high temperature co-fired ceramic, HTCC, or a low temperature co-fired ceramic, LTCC.

This embodiment provides a relatively simple and low-cost reproducible method of production of the ceramic heating element.

In an embodiment of the electronic cigarette, the heating member comprises at least one of titanium, tungsten, molybdenum, and molybdenum-manganese alloy.

It has been found that these metals/metal alloys can be combined with a body of ceramic material to produce a ceramic heating element excellently suited for use in an electronic cigarette. At least some of these metals/metal alloys can be applied in a 3-D printing process on the ceramic material before or after further processing thereof to form the body of ceramic material.

In a second aspect of the present invention, a method of cleaning the electronic cigarette according to an embodiment of the first aspect is provided. The method comprises: moving the battery holding part and the cartomizer part apart, whereby liquid delivered by the liquid delivery member is not vaporized when the ceramic heating element produces heat; and electrically connecting the battery to the ceramic heating element for the heating element to produce heat.

In a third aspect of the present invention, a method of cleaning the electronic cigarette, wherein the battery holding part of the electronic cigarette comprises an electric connector between the ceramic heating element and the electric circuit. The method comprises moving the battery holding part and the cartomizer part apart, removing the ceramic heating element from the battery holding part, and mounting another ceramic heating element in the battery holding part.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
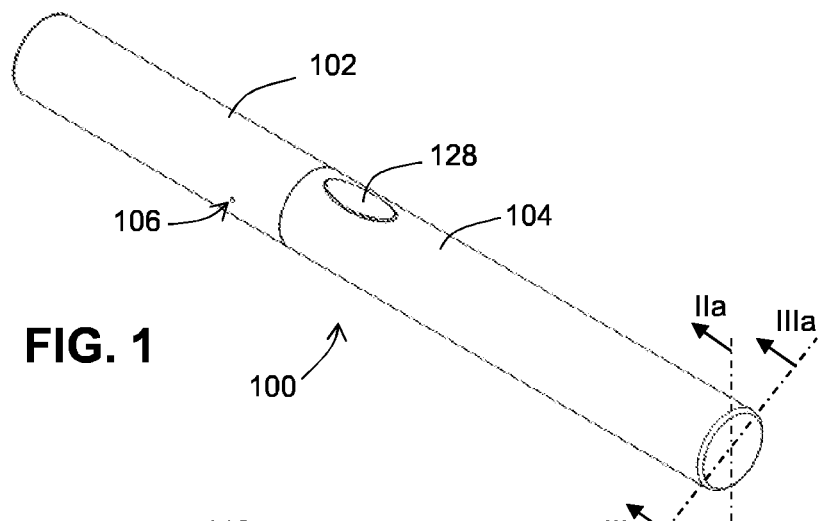
FIG. 1 depicts an isometric view of an embodiment of an electronic cigarette of the present invention.
Figure 2A:
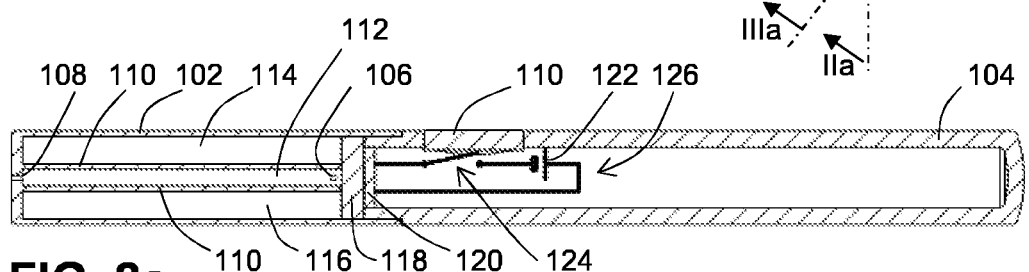
FIG. 2a depicts a longitudinal cross-sectional view of the electronic cigarette of FIG. 1, taken along a plane IIa indicated in FIG. 1, wherein a battery, an electric switch, and an electric circuit are schematically indicated.
Figure 3A:
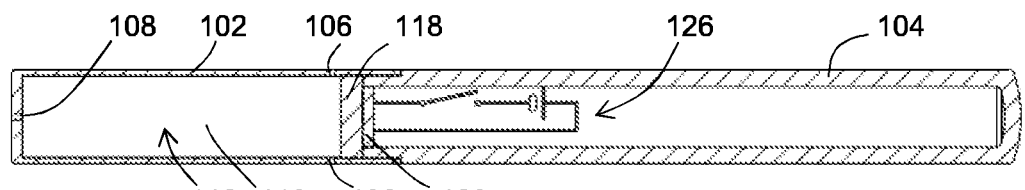
FIG. 3a depicts a longitudinal cross-sectional view of the electronic cigarette of FIG. 1, taken along a plane IIIa indicated in FIG. 1, wherein a battery, an electric switch, and an electric circuit are schematically indicated.

FIGS. 1, 2a, and 3a depict an electronic cigarette 100 comprising a cartomizer part 102 and a battery holding part 104.

Figure 2B:
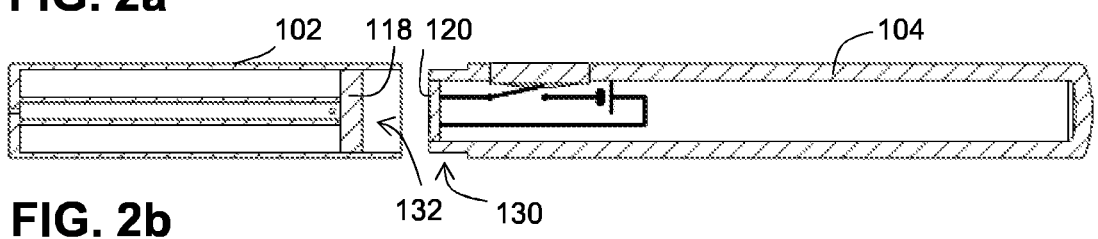
FIG. 2b depicts the longitudinal cross-sectional view of the electronic cigarette of FIG. 2a in a disassembled state.

The cartomizer part 102 is provided with two air inlet holes 106 located opposite to each other (only one air inlet hole visible in FIGS. 1, 2a and 2b). The cartomizer part 102 comprises an air/vapor outlet hole 108 at an end of the cartomizer part 102 serving as a mouthpiece portion of the electronic cigarette 100. Two parallel walls 110 define a duct 112 providing a flow path for a flow of air and vapor from the air inlet holes 106 to the air/vapor outlet hole 108. The walls 110 and the outer wall of the cartomizer part 102 further delimit spaces 114, 116 to store liquid.

The cartomizer part 102 further comprises a liquid delivery member 118 made from a porous material, such as made from fibers or from a porous ceramic or other heat-resistant material. The liquid delivery member 118 is configured to deliver liquid from the liquid storage spaces 114, 116 to a heating element 120. One side of the liquid delivery member 118 forms one end of the duct 112. An opposite side of the liquid delivery member 118 is configured to face the heating element 120. The heating element 120 is a ceramic heating element comprising a current conducting heating member on and/or in a body of ceramic material which is impenetrable to the liquid contained in the spaces 114, 116 and the liquid delivery member 118 of the cartomizer part 102.

The battery holding part 104 comprises a battery 122, diagrammatically indicated in the Figures, and an electric switch 124, also diagrammatically indicated in the Figures, which electric switch 124 is operable to electrically connect the battery 122 to the ceramic heating element 120, and to electrically disconnect the battery 122 from the ceramic heating element 120. The electric switch 124 is part of an electric circuit 126 configured to electrically connect the ceramic heating element 120 to the battery 122 for the ceramic heating element 120 to produce heat, and to electrically disconnect the battery 122 from the ceramic heating element 120. The electric switch 124 may be embodied in a manner known per se.

Figure 4:
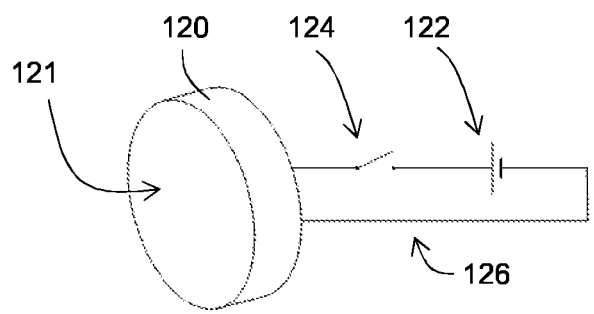
FIG. 4 depicts an isometric view of an embodiment of the ceramic heating element of the electronic cigarette of the present invention, wherein a battery, an electric switch, and an electric circuit are schematically indicated.

FIG. 4 shows the ceramic heating element 120 in a perspective view, with the electric circuit 126 comprising the electric switch 124 connecting the battery 122 to the ceramic heating element 120 may be cylinder-shaped, having a side 121 configured to be facing the liquid delivery member 118, which may also be cylinder-shaped. However, various other forms of ceramic heating element and liquid delivery member may be contemplated to produce the same or similar effects as described in this disclosure.

The body of ceramic material of the ceramic heating element 120 preferably comprises aluminum nitride, AlN, alumina, Al2O3, or silicon nitride, Si3N4. The ceramic heating element 120 preferably is manufactured in a co-fired process such that the ceramic heating element 120 comprises a co-fired ceramic, in particular a high temperature co-fired ceramic, HTCC, or a low temperature co-fired ceramic, LTCC. The heating member of the ceramic heating element 120 preferably comprises at least one of titanium, tungsten, molybdenum, and a molybdenum-manganese alloy. The ceramic heating element 120 has a positive temperature coefficient of electrical resistance to limit the temperature of the ceramic heating element 120 when it is activated, by self-stabilization.

In the embodiment shown in the Figures, the electric switch 124 can be manually operated by a button 128. In a manner known per se, the button 128 may be pressed to close the electric switch 124 to activate the ceramic heating element 120 to produce heat generated by a current flowing in the electric circuit 126 from the battery 122. Once released, the button 128 may resume its initial position, whereby the electric switch 124 is opened to deactivate the ceramic heating element 120 by interrupting the current flowing in the electric circuit 126 from the battery 122. In other embodiments, the electric switch 124 may be operated through a control circuit comprising a flow sensor to detect a user action of drawing in air through the duct 112. For example, upon detection of air flow by the flow sensor, the control circuit closes the electric switch 124, and upon detection of absence of air flow by the flow sensor, the control circuit opens the electric switch 124.

The battery 122 may take different shapes, and may be a disposable, non-rechargeable battery, or may be a rechargeable battery. In the latter case, the electronic cigarette 100, in particular the battery holding part 104, may be provided with a connector (not shown) to directly power the battery 122 from a power source, or to indirectly power the battery 122 from a power source, possibly wirelessly by inductive coupling, through an internal charging circuit (not shown) connected to the battery 122.

Figure 3B:
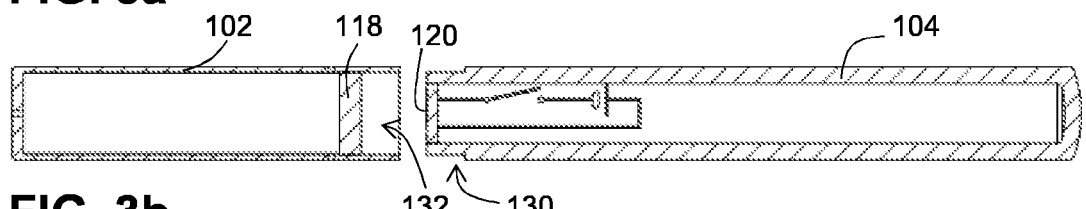
FIG. 3b depicts the longitudinal cross-sectional view of the electronic cigarette of FIG. 3a in a disassembled state.

In FIGS. 2a and 3a, the battery holding part 104 is coupled, i.e. connected, to the cartomizer part 102. This can be regarded as an assembled state of the electronic cigarette 100. In FIGS. 2b and 3b, the battery holding part 104 is decoupled, i.e. separated, from the cartomizer part 102. This can be regarded as a disassembled state of the electronic cigarette 100. The electronic cigarette 100 is provided with a separating structure shaped as a male coupling portion 130 provided on the battery holding part 104, and adapted to be coupled to a female coupling portion 132 provided on the cartomizer part 102.

In the assembled state of the electronic cigarette 100, when the male coupling portion 130 has been inserted into the female coupling portion 132, the ceramic heating element 120, in particular its body of ceramic material, is in contact with the liquid delivery member 118, or is in close proximity to the liquid delivery member 118, such that the body of ceramic material is configured to heat the liquid delivered by the liquid delivery member 118 to vaporize the liquid when the ceramic heating element 120 produces heat through closing of the electric switch 124, in this embodiment by pressing the button 128. The vaporized liquid emerges at the side of the liquid delivery member 118 facing the duct 112, where the vapor can be inhaled by the user of the electronic cigarette 100 through the air/vapor outlet 108.

In the disassembled state of the electronic cigarette 100, when the male coupling portion 130 has been removed from the female coupling portion 132, the ceramic heating element 120, in particular its body of ceramic material, and the liquid delivery member 118 have been moved away from each other to a distance at which the liquid delivered by the liquid delivery member 118 is not vaporized when the ceramic heating element 120 produces heat through closing of the electric switch 124, in this embodiment by pressing the button 128.

Figure 5:
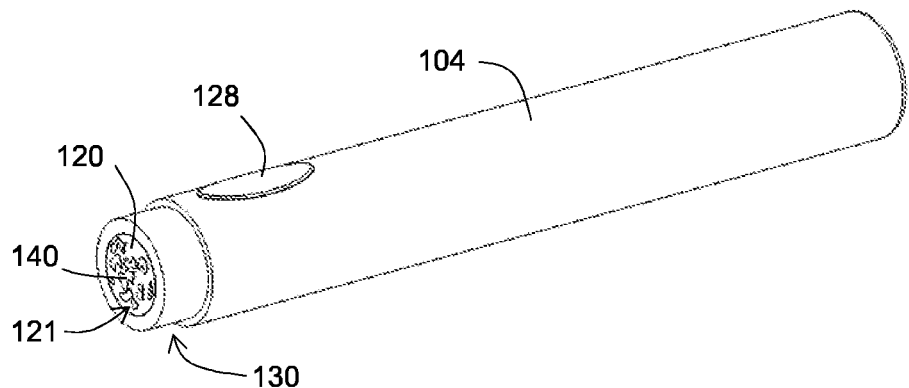
FIG. 5 depicts an isometric view of a battery holding part of the electronic cigarette of the present invention, showing pollution stains of burnt liquid on the ceramic heating element.
Figure 6:
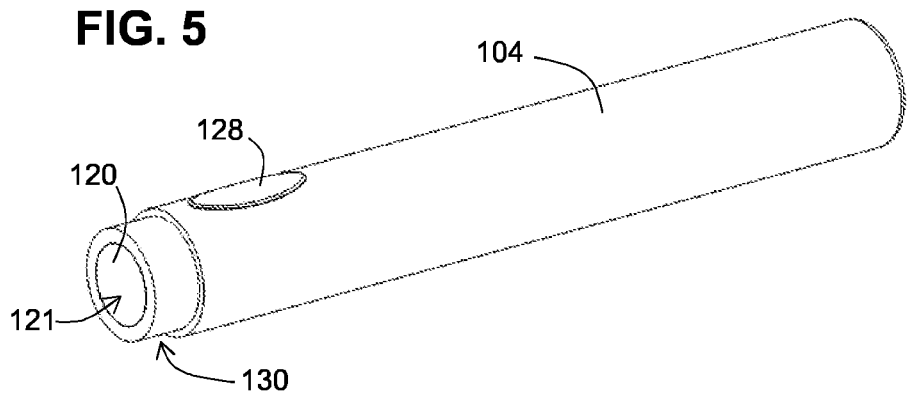
FIG. 6 depicts an isometric view of the battery holding part of FIG. 5, showing the ceramic heating element after removal of the stains.

As seen in FIG. 5, stains of pollution 140 form on side 121 of the ceramic heating element 120 in the course of time of use of the electronic cigarette 100, wherein the pollution 140 comprises burnt vaporizing liquid. The activation of the ceramic heating element 120 to produce heat in the disassembled state of the electronic cigarette 100 quickly, within seconds, leads to an evaporation of pollution 140 on side 121 of ceramic heating element 120, as illustrated in FIG. 6.

Thus, the ceramic heating element 120 can be easily cleaned without any further cleaning means.

It is noted that the heating element is not contained in the cartomizer part 102. Accordingly, the cartomizer part 102, only comprising a liquid storage 114, 116 and a liquid delivery member 118, can be manufactured at low cost, and may for the convenience of the user be treated as a disposable part. The more expensive components of the electronic cigarette 100, such as the battery 122 and the ceramic heating element 120, are contained in the battery holding part 104, and can be re-used with different cartomizer parts 102.

Figure 7A:
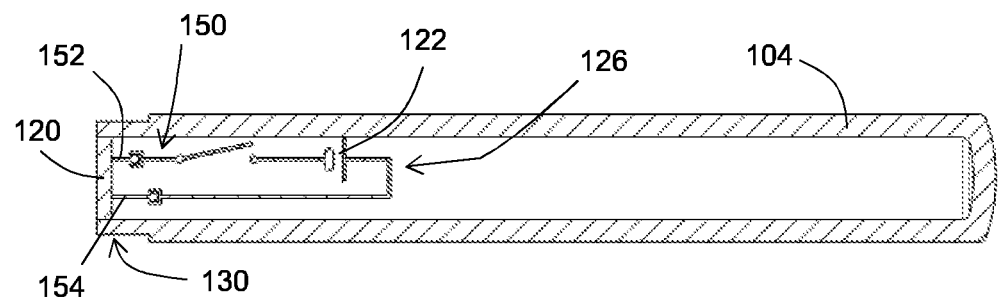
FIG. 7a depicts a longitudinal cross-sectional view of a further embodiment of a battery holding part of the electronic cigarette of the present invention.
Figure 7B:
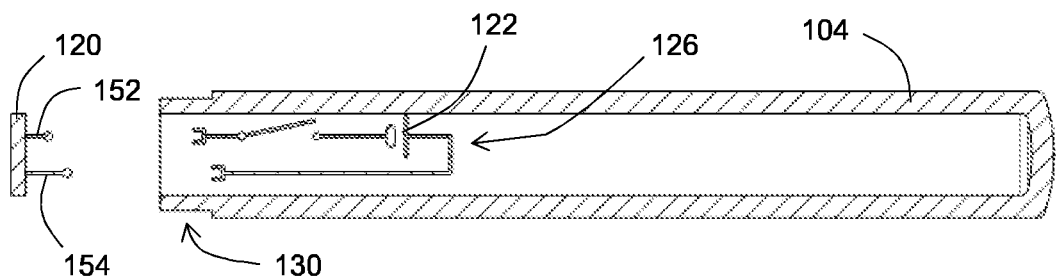
FIG. 7b depicts the longitudinal cross-sectional view of the battery holding part of FIG. 7a in a disassembled state.

FIG. 7a depicts the battery holding part 104 comprising the battery 122 in the electric circuit 126. The electric circuit 126 comprises an electric connector 150 which is configured to mechanically and electrically connect the ceramic heating element 120 to the electric circuit 126 when the ceramic heating element 120 is mounted in the battery holding part 104. The electric connector 150 further is configured to disconnect the ceramic heating element 120 from the electric circuit 126 when the ceramic heating element 120 is removed from the battery holding part 104, as illustrated in FIG. 7b. The electric connector 150 comprises interengageable male and female connecting parts, whereby electric terminals 152, 154 of the ceramic heating element 120 may be electrically and mechanically coupled to, and decoupled from, the electric circuit 126. The electric connector 150 may also comprise at least one spring element that pushes at least one contact of the battery side connector part of the electric connector 150 against at least one contact of the ceramic heating element side of the electric connector 150 (as may be seen, for example, with these and other uses of an alkaline battery).

Figure 8:
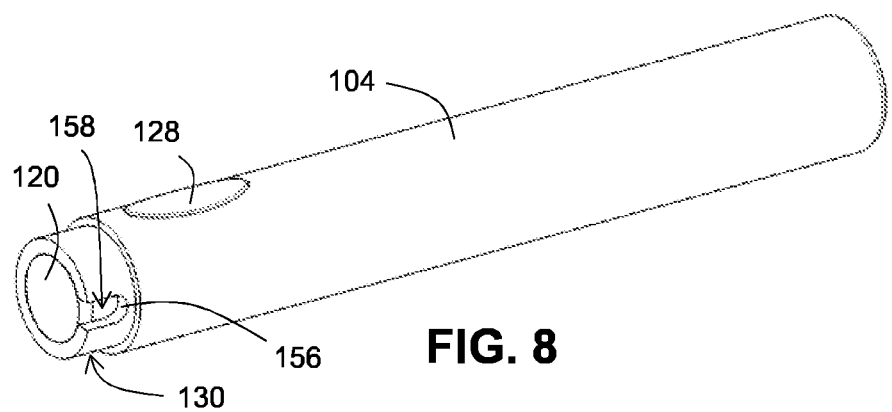
FIG. 8 depicts an isometric view of the battery holding part of FIGS. 7a and 7b, including a ceramic heating element removal structure.

As illustrated in FIG. 8, the battery holding part 104, comprising the electric connector 150, may comprise a ceramic heating element removal structure for facilitating a removal of the ceramic heating element 120 from the battery holding part 104. The ceramic heating element 120, in the embodiment shown to be substantially cylindrically shaped, may be clamped in an opening, such as an end opening, of the battery holding part 104. In the opening, the ceramic heating element 120 is held by friction, and the electric terminals 152, 154 of the ceramic heating element 120 are held by friction by the electric connector 150. The ceramic heating element removal structure may comprise a hole or recess 156 in the male coupling portion 130 of the battery holding part 104 for inserting a tool into opening 158 behind the ceramic heating element 120 to move the ceramic heating element 120 out of the opening of the battery holding part 104 (as illustrated in FIG. 7b), thereby releasing the electric terminals 152, 154 of the ceramic heating element 120 from the connector 150.

As explained in detail above, an electronic cigarette comprises: a liquid storage; a heating element; a liquid delivery member configured to deliver liquid from the liquid storage to the heating element; a battery; and an electric circuit for electrically connecting the heating element to the battery. The heating element is a ceramic heating element comprising a current conducting heating member on and/or in a body of ceramic material which is impenetrable to the liquid. The body of ceramic material is to contact the liquid delivery member, or to be in close proximity to the liquid delivery member, to heat the liquid delivered by the liquid delivery member to vaporize the liquid when the ceramic heating element produces heat. The electronic cigarette comprises a cartomizer part, comprising the liquid storage and the liquid delivery member, and a battery holding part, comprising the battery, the ceramic heating element, and the electric circuit. In an assembled state of the electronic cigarette, the cartomizer part and the battery holding part are assembled. In a disassembled state, the cartomizer part and the battery holding part are separated from one another.

Detailed embodiments of the present invention are disclosed herein. However, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in any appropriately detailed structure. Further, the terms and phrases used herein are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures is excluded. On the contrary, appropriate advantageous combinations of these measures may be made.

The invention claimed is:

1. An electronic cigarette, comprising:
   a liquid storage;
   a heating element;
   a liquid delivery member configured to deliver liquid from the liquid storage to the heating element;
   a battery; and
   an electric circuit configured to electrically connect the heating element to the battery for the heating element to produce heat, and further configured to electrically disconnect the battery from the heating element,
   wherein the heating element is a ceramic heating element comprising a current conducting heating member on and/or in a body of ceramic material,
   wherein the body of ceramic material is configured to heat the liquid delivered by the liquid delivery member to vaporize the liquid when the ceramic heating element produces heat, and
   wherein the electronic cigarette further comprises a cartomizer part and a battery holding part, the electronic cigarette being configured to be brought in an assembled state in which the cartomizer part and the battery holding part are assembled, and further being configured to be brought in a disassembled state in which the cartomizer part and the battery holding part are separated from one another,
   wherein the cartomizer part comprises the liquid storage and the liquid delivery member; and
   wherein the battery holding part comprises the battery, the ceramic heating element, and the electric circuit.

2. The electronic cigarette of claim 1, wherein the body of ceramic material is configured to contact the liquid delivery member.

3. The electronic cigarette of claim 1, further comprising a separating structure for moving the body of ceramic material and the liquid delivery member away from each other to a distance at which the liquid delivered by the liquid delivery member is not vaporized when the ceramic heating element produces heat.

4. The electronic cigarette of claim 1, wherein the electric circuit comprises an electric switch operable to electrically connect the battery to the ceramic heating element, and further operable to electrically disconnect the battery from the ceramic heating element.

5. The electronic cigarette of claim 1, wherein the ceramic heating element has a positive temperature coefficient of electrical resistance.

6. The electronic cigarette of claim 1, wherein the ceramic material comprises aluminum nitride, alumina, or silicon nitride.

7. The electronic cigarette of claim 1, wherein the ceramic heating element comprises a co-fired ceramic.

8. The electronic cigarette of claim 1, wherein the current conducting heating member comprises at least one of titanium, tungsten, molybdenum, and molybdenum-manganese alloy.

9. The electronic cigarette of claim 1, wherein the body of ceramic material is impenetrable to the liquid.

10. The electronic cigarette of claim 1, wherein the electric circuit comprises an electric connector, and wherein the electric connector is configured to connect the ceramic heating element to the electric circuit when the ceramic heating element is mounted in the battery holding part, and wherein the electric connector is further configured to disconnect the ceramic heating element from the electric circuit when the ceramic heating element is removed from the battery holding part.

11. The electronic cigarette of claim 10, wherein the battery holding part comprises a ceramic heating element removal structure for facilitating a removal of the ceramic heating element from the battery holding part.

12. A method of cleaning the electronic cigarette of claim 1, the method comprising:
   moving the battery holding part and the cartomizer part apart, whereby liquid delivered by the liquid delivery member is not vaporized when the ceramic heating element produces heat; and
   electrically connecting the battery to the ceramic heating element for the heating element to produce heat.

13. A method of cleaning the electronic cigarette of claim 10, the method comprising:
   moving the battery holding part and the cartomizer part apart;
   removing the ceramic heating element from the battery holding part; and
   mounting another ceramic heating element in the battery holding part.

* * * * *